United States Patent
Otsuka et al.

(10) Patent No.: US 10,596,265 B2
(45) Date of Patent: Mar. 24, 2020

(54) SYNTHESIS OF NANO AGGREGATE OF CHITOSAN MODIFIED BY SELF-ASSEMBLING PEPTIDE AND APPLICATION THEREOF TO PROTEIN DELIVERY

(71) Applicants: 3-D Matrix, Ltd., Tokyo (JP); Tokyo University of Science Foundation, Tokyo (JP)

(72) Inventors: Hidenori Otsuka, Tokyo (JP); Daisuke Matsukuma, Tokyo (JP)

(73) Assignees: 3-D Matrix, Ltd., Tokyo (JP); Tokyo University of Science Foundation, Tokyo (JP)

( * ) Notice: Subject to any disclaimer, the term of this patent is extended or adjusted under 35 U.S.C. 154(b) by 0 days.

(21) Appl. No.: 15/526,633

(22) PCT Filed: Aug. 24, 2015

(86) PCT No.: PCT/JP2015/073745
§ 371 (c)(1),
(2) Date: May 12, 2017

(87) PCT Pub. No.: WO2016/075977
PCT Pub. Date: May 19, 2016

(65) Prior Publication Data
US 2017/0312370 A1 Nov. 2, 2017

(30) Foreign Application Priority Data

Nov. 14, 2014 (JP) .................................. 2014-231447

(51) Int. Cl.
| | | |
|---|---|---|
| A61K 38/00 | (2006.01) | |
| A61K 47/42 | (2017.01) | |
| A61K 47/34 | (2017.01) | |
| A61K 47/36 | (2006.01) | |

(52) U.S. Cl.
CPC .............. *A61K 47/42* (2013.01); *A61K 47/34* (2013.01); *A61K 47/36* (2013.01); *A61K 38/00* (2013.01)

(58) Field of Classification Search
CPC ........ A61K 38/00; A61K 47/34; A61K 47/36; A61K 47/42
USPC .................................................. 530/300, 326
See application file for complete search history.

(56) References Cited

U.S. PATENT DOCUMENTS 8,022,178 B2 * 9/2011 Horii ...................... A61L 27/227
530/324
2014/0178455 A1 * 6/2014 Nukavarapu ........... A61L 27/58
424/426

FOREIGN PATENT DOCUMENTS

| JP | 2011-012042 A | 1/2011 |
| WO | 2014/133027 A1 | 9/2014 |

OTHER PUBLICATIONS

Jiang et al, "Click hydrogel, microgels and nanogels: Emerging platforms for drug delivery and tissue engineering," Biomaterials, Mar. 24, 2014, 35: 4969-4985.*
Jiang et al, "Click hydrogels, microgels and nanogels: Emerging platforms for drug delivery and tissue engineering," Biomaterials, 2014, 35: 4969-4985.*
Sahiner et al, "Microgel, nanogel and hydrogel-hydrogel semi-IPN composites for biodmeical applications: synthesis and characterization," Colloid Polym Sci, 2006, 284: 1121-1129.*
International Search Report and Written Opinion for Application No. PCT/JP2015/073745, dated Nov. 10, 2015 (10 pages, with Engl. translation of Search Report).
Matsukuma, D., et al., "3D Scaffold," CSJ: The Chemical Society of Japan Dai 93 Shunki Nenkai 2013 Nen Koen Yokoshu III, 2013, p. 845 (Abstract Only).
Zhang, H., et al., "Mechanistic Study of Self-Assembling Peptide RADA16-I in Formation of Nanofibers and Hydrogels," J. Nanotech. Eng. Med., 2010, v. 1, pp. 11007.1-11007.6.

* cited by examiner

*Primary Examiner* — Julie Ha
(74) *Attorney, Agent, or Firm* — Constantine Linnik IP Supra, PLLC

(57) ABSTRACT

A nanogel comprising a self-organizing peptide, a chitosan and polyethylene glycol is described.

1 Claim, 12 Drawing Sheets
Specification includes a Sequence Listing.

| | Grafted degree /% | | |
|---|---|---|---|
| | PEG a) | HL a) | RADA16 b) |
| PEG/RADA-g-CS c) | 12 | 40 | 35 | a) Calculated by $^1$H-NMR. b) Estimated by micro BCA assay.
c) The deacetylation degree of CS is 54%

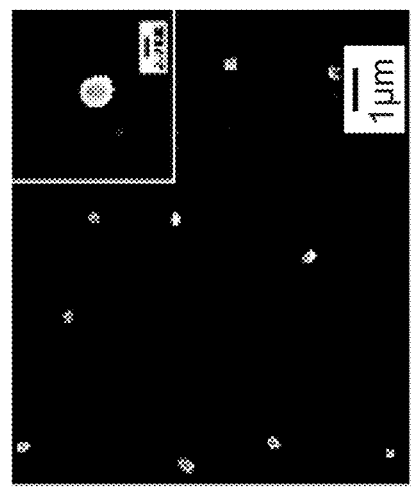
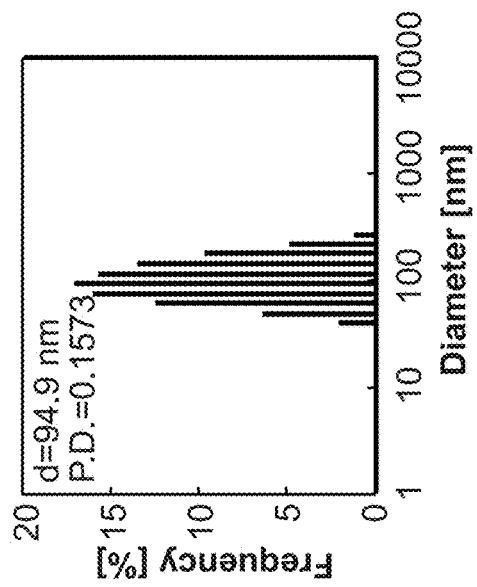
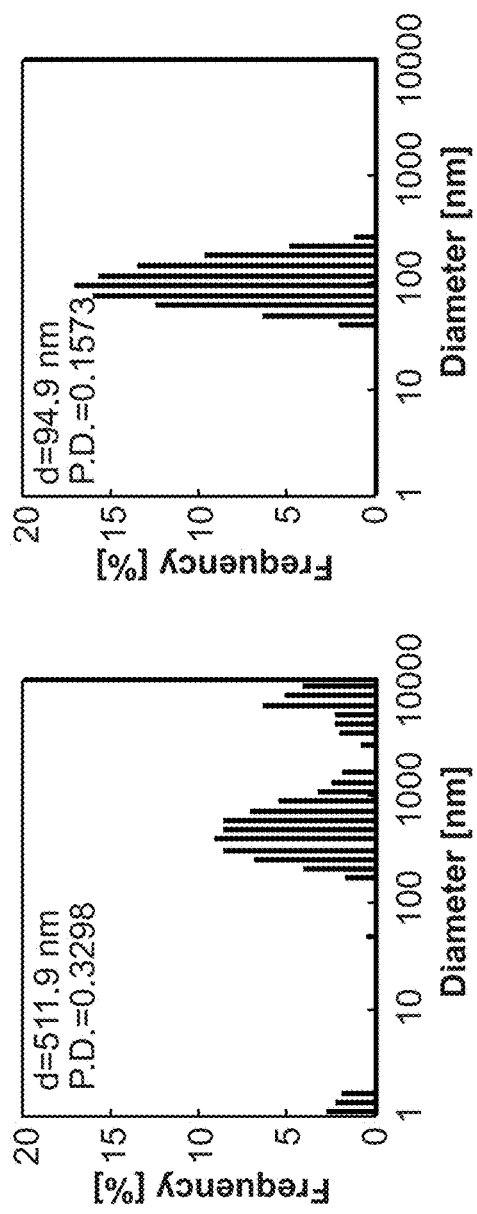
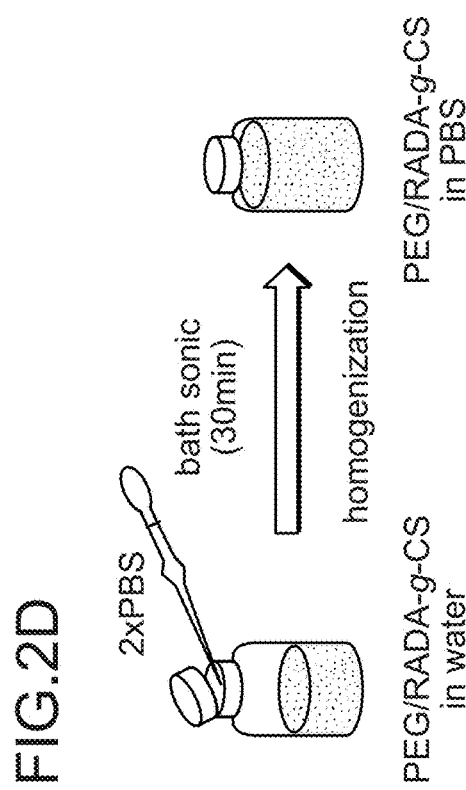

FIG. 3A
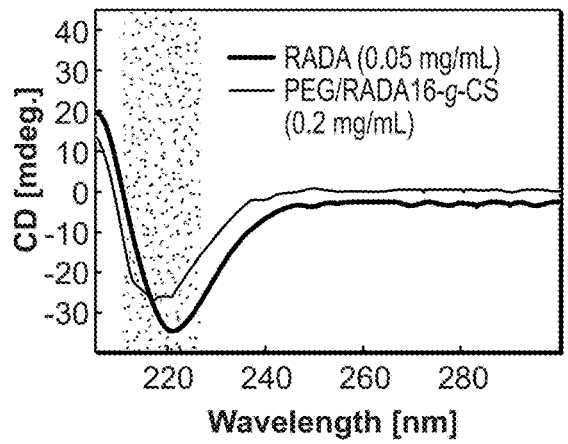
FIG. 3B
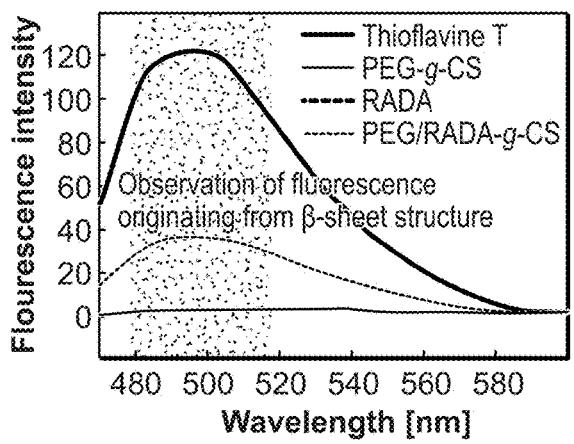
FIG. 4A
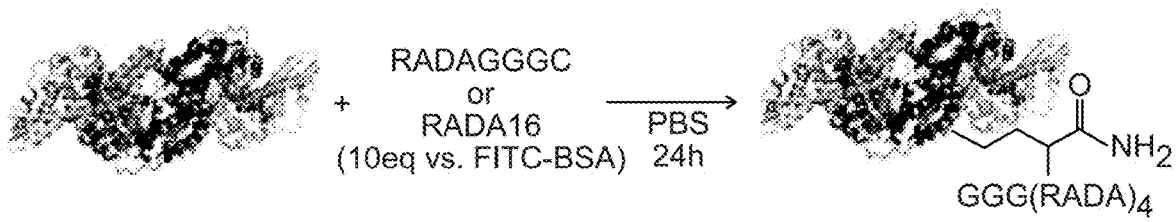
FIG. 4B
| sample name | FITC-BSA concentration [mg/mL] | FITC-BSA state |
| --- | --- | --- |
| Free | | FITC-BSA mixed with nothing |
| RADA | 0.4 | Mixed with RADA16 |
| GGGC | | Mixed with RADAGGGC |

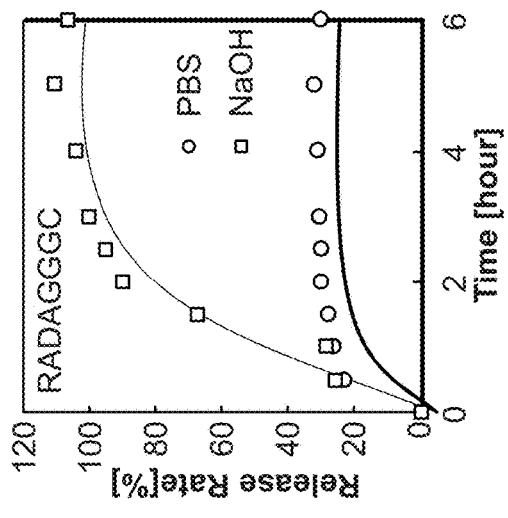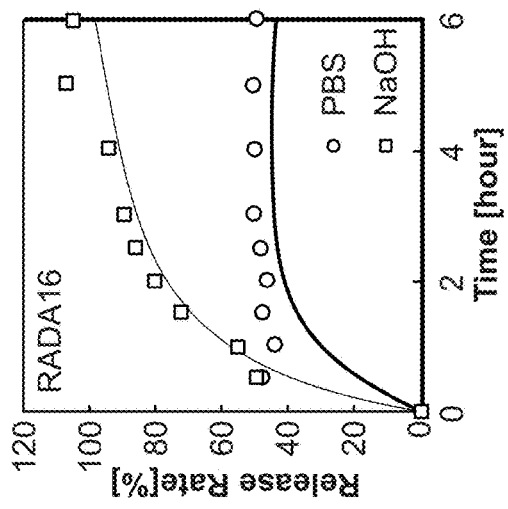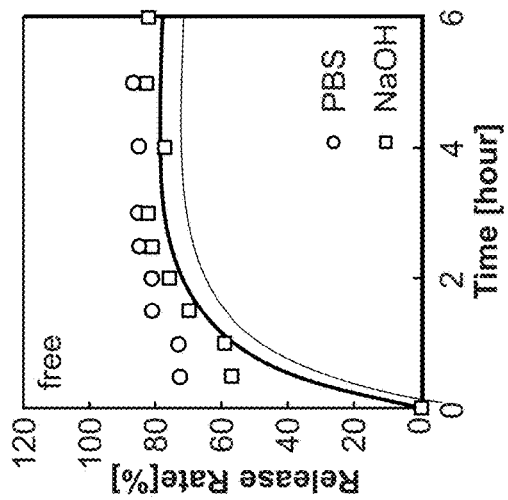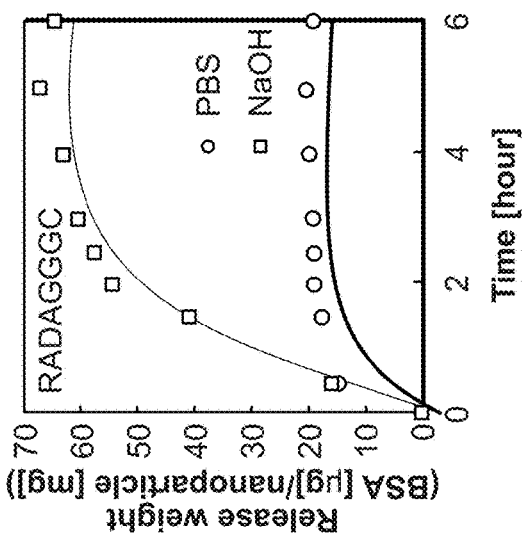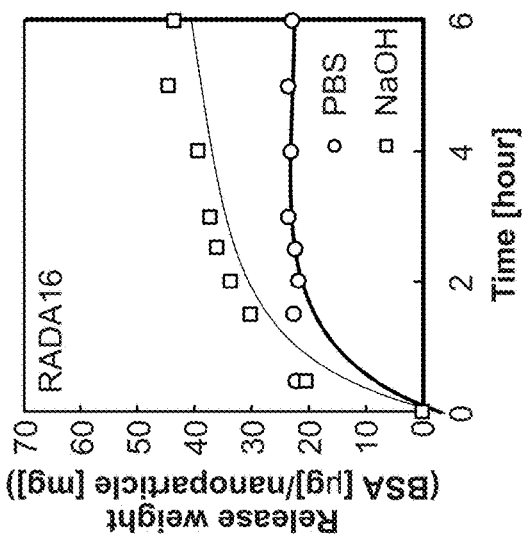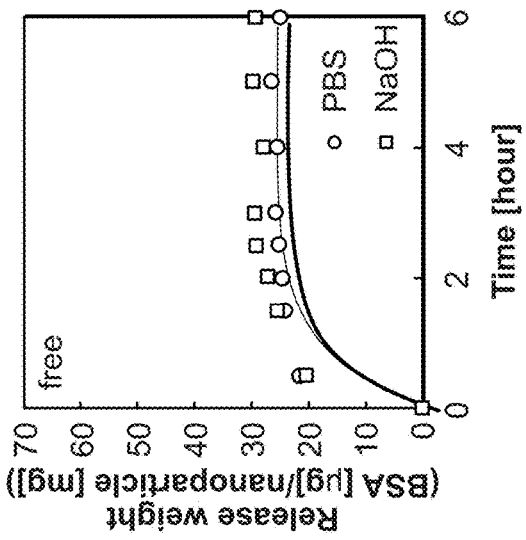

SYNTHESIS OF NANO AGGREGATE OF CHITOSAN MODIFIED BY SELF-ASSEMBLING PEPTIDE AND APPLICATION THEREOF TO PROTEIN DELIVERY

CROSS-REFERENCE TO RELATED APPLICATIONS

This application is a U.S. National Stage Application of PCT/JP2015/073745 filed on Aug. 24, 2015. PCT/JP2015/073745 claims priority of JP 2014-231447 filed on Nov. 14, 2014. The contents of these applications are all herein incorporated by reference in their entirety.

SEQUENCE LISTING

The instant application contains a Sequence Listing which has been submitted electronically in ASCII format and is hereby incorporated by reference in its entirety. Said ASCII copy, created on May 11, 2017 is named 117146-109_ST25.txt and is 1029 bytes in size.

FIELD OF INVENTION

The present invention relates to a nanogel comprising a self-organizing peptide, a chitosan, and polyethylene glycol.

BACKGROUND

With the recent focus on drug delivery systems (DDS) using bioactive proteins as medicinal products, there have been numerous studies on functional carriers for maintaining effective pharmacological activity of bioactive proteins. However, denaturing and low encapsulation efficiency of proteins on carriers remain as major problems, and there is a need for a carrier design that increases encapsulation efficiency but does not harm the stereoscopic structure of proteins.

SUMMARY OF THE INVENTION

Self-organizing peptides having certain amino acid sequences build self-organizing networks based on β-sheet structure formation. It is believed that if a nanocarrier that uses a self-organizing network of peptides having excellent biocompatibility as a carrier matrix can be created, it will result in a novel DDS carrier capable of maintaining the structural stability of proteins. The present invention provides a novel DDS carrier capable of maintaining the structural stability of proteins. The nanogel of the present invention has excellent sustained release characteristics without harming the function of a protein.

In various aspects, the invention provides a drug delivery system comprising a bioactive protein and a nanogel encapsulating the bioactive protein, the nanogel comprising a self-organizing peptide, a chitosan, and polyethylene glycol.

In various aspects, the invention provides a method of delivering a bioactive protein to a target site in a subject, the method comprising administering an effective amount of the drug delivery system to the target site in the subject.

It will be understood by those skilled in the art, any of the aspects above can be combined with any one or more of the features below.

In various embodiments, the self-organizing peptide is RADARADARADARADA (SEQ ID NO: 1) or RADARADARADAGGGC (SEQ ID NO: 2).

In various embodiments, the self-organizing peptide comprises Formula I, II, III, or IV: ((XY)l-(ZY)m)n is Formula I, ((YX)l-(YZ)m)n Formula II, ((ZY)l-(XY)m)n Formula III, ((YZ)l-(YX)m)n Formula IV, wherein each X is independently an acidic amino acid, wherein each Y is independently a hydrophobic amino acid, wherein each Z is independently a basic amino acid, wherein each 1, m, and n are integers such that n×(1+m)<200.

In various embodiments, the self-organizing peptide is RADARADARADAGGGC (SEQ ID NO: 2).

In various embodiments, the chitosan comprises deacetylated chitin.

In various embodiments, the chitosan comprises a β-1,4-polyglucosamine.

In various embodiments, the chitosan is derivatised.

In various embodiments, the chitosan has a weight-average molecular weight between 1000 and 1,000,000 g/mol.

In various embodiments, the chitosan has a weight-average molecular weight between 10,000 and 300,000 g/mol.

In various embodiments, a deacetylation degree of the chitosan is about 50%.

In various embodiments, the polyethylene glycol is derivatised.

In various embodiments, the polyethylene glycol has a molecular weight between 1000 and 20,000 g/mol.

In various embodiments, the polyethylene glycol has a molecular weight between 1000 and 5000 g/mol.

These and other advantages of the present technology will be apparent when reference is made to the following description.

BRIEF DESCRIPTION OF THE DRAWINGS

FIGS. 2A-2B present examples of aggregation behavior of PEG/RADA-g-CS.

FIG. 2C presents an example of scanning electron microscope image of aggregates formed in 2B.

FIG. 2D presents a process of preparing PEG/RADA-g-CS samples for evaluating aggregation behavior shown in FIGS. 2A-2C.

FIG. 3A presents an example of evaluation of β-sheet structure in PEG/RADA-g-CS using a CD spectrum measurement.

FIG. 3B presents an example of evaluation of β-sheet structure in PEG/RADA-g-CS using a fluorescence intensity measurement.

FIGS. 4A-4B present examples of evaluation of encapsulation and release behavior of FITC-BSA on PEG/RADA-g-CS aggregate.

FIGS. 9A-9F present examples of FITC-BSA release behavior.

DETAILED DESCRIPTION

Figures 1A, 1B:
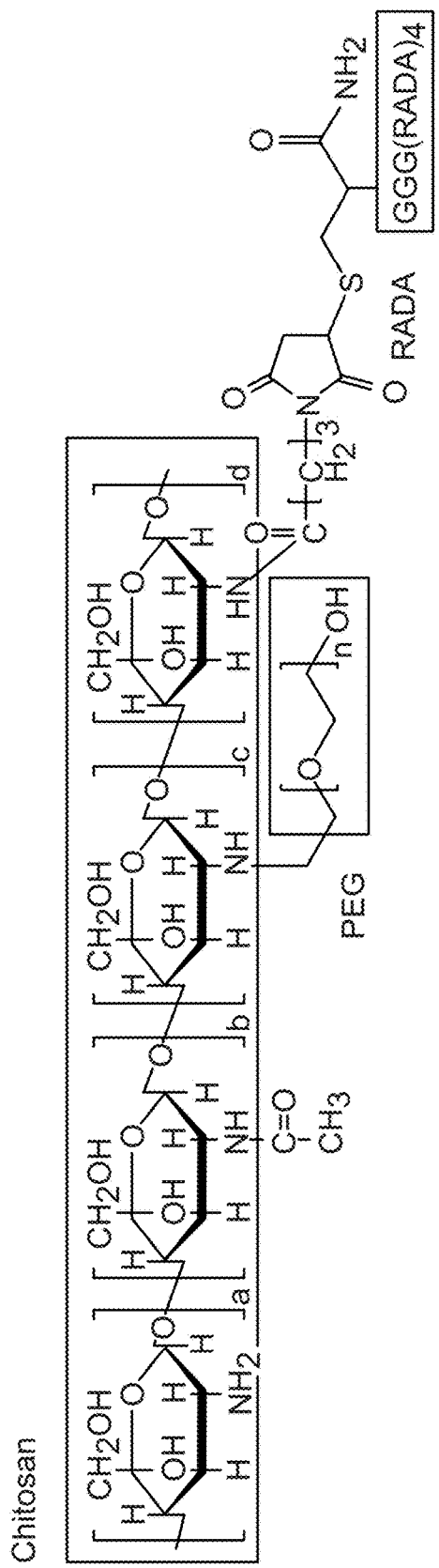
FIG. 1A presents an example structure of PEG/RADA-g-CS.
FIG. 1B presents an example proportion of modification of PEG and RADA relative to amino acid groups in the chitosan.

The self-organizing peptide used in the present invention may be represented by any of the following four general formulas.

$$((XY)l\text{-}(ZY)m)n \quad (I)$$

$$((YX)l\text{-}(YZ)m)n \quad (II)$$

$$((ZY)l\text{-}(XY)m)n \quad (III)$$

$$((YZ)l\text{-}(YX)m)n \quad (IV)$$

(In formulas (I) to (IV), X represents an acidic amino acid, Y represents a hydrophobic amino acid, Z represents a basic amino acid, and 1, m, and n are integers wherein n×(1+m) <200.)

The N-terminus thereof may be acetylated, and the C-terminus may be amidated.

Here, hydrophilic amino acids that may be used are acidic amino acids selected from aspartic acid and glutamic acid, and basic amino acids selected from arginine, lysine, histidine, and ornithine. Hydrophobic acids that may be used are alanine, valine, leucine, isoleucine, methionine, phenylalanine, tyrosine, tryptophan, serine, threonine, and glycine.

Among these self-organizing peptides, those having a repeating sequence of arginine, alanine, aspartic acid, and alanine (RADA) are preferably used. More specifically, RADARADARADARADA (PuraMatrix®) (SEQ ID NO: 1), or RADARADARADARADAGGGC (RADAGGGC) (SEQ ID NO: 2), which is an end-modified form thereof, may be used.

Chitosan is a deacetylation product of chitin (β-1,4-poly-N-acetylglucosamine), and is a polysaccharide having mainly a β-1,4-polyglucosamine structure. The chitosan of the present invention includes conventionally known derivatives, e.g., carboxymethylchitosan.

The chitosan can be prepared by any method known in this field. For example, the chitosan may be obtained by deacetylation by alkali treatment (e.g., caustic soda treatment) of chitin obtained by decalcium treatment and deproteinization treatment of a raw material such as the shells of crustaceans such as crab, shrimp, and krill, or the shells of insects such as beetles and grasshoppers. Furthermore, instead of the aforementioned shells, the chitosan raw material may be mushrooms, microbes, squid backbone, etc.

Chitosans of various molecular weights are known. In the aqueous composition of the present invention, the molecular weight of the chitosan is not particularly limited, but the weight-average molecular weight is preferably from 1000 to 1,000,000, and more preferably from 10,000 to 300,000. Weight-average molecular weight can also be called "weight-average absolute molecular weight."

The weight-average molecular weight of chitosan can be measured by any method known in this field. For example, the weight-average molecular weight may be measured by methods such as gel permeation chromatography-multiangle laser light scattering (GPC-MALS), absolute molecular weight measurement by vapor pressure, or absolute molecular weight measurement by membrane. The weight-average molecular weight of the chitosan should be within the aforementioned range of numeric values when using at least one of the measurement methods and measurement conditions, but does not have to be within the aforementioned range of numeric values when using all of the measurement methods and measurement conditions.

In the chitosan contained in the aqueous composition of the present invention, the deacetylation degree from chitin is preferably approximately 50%.

The polyethylene glycol of the present invention includes conventionally known derivatives, e.g., multiarm polyethylene glycols and derivatives terminated with an amino group-reactive structure such as an aldehyde, hydroxysuccinimide ester, or nitrobenzene sulfonate ester structure. The molecular weight of the polyethylene glycol is preferably from 1000 to 20,000, and more preferably from 1000 to 5000.

The term "polymer" means a molecule that can be obtained from monomers having a low molecular weight and has a structure constituted of repeating monomer units. The term "macromolecule" means a giant molecule in which a large number of atoms are covalently bonded, such as proteins and nucleic acids.

For polymers, the term "average degree of polymerization" means the average number of monomer units contained in one polymer molecule. That is, polymer molecules of differing lengths are dispersed in a polymer composition in a certain range.

"Number-average molecular weight" in regard to the degree of polymerization of a polymer means the average of the molecular weight per molecule in a polymer composition, and "weight-average molecular weight" means the molecular weight calculated by weighting the weights. Furthermore, the ratio of weight-average molecular weight to number-average molecular weight is called dispersity, which serves as a measure of the molecular weight distribution in a polymer composition. As dispersity approaches 1, the average degree of polymerization in a polymer composition gets closer, meaning it contains many polymer chains of approximately the same length.

In the nanogel of the present invention, additives may also be added as necessary within a range that does not deviate from the spirit of the present invention. For example, additives such as radical scavengers, peroxide decomposers, antioxidants, UV absorbents, heat stabilizers, plasticizers, flame retardants, antistatic agents, etc. may be used. Additionally, polymers other than the polymer of the present invention may be mixed in. Such compositions containing the biodegradable nanogel of the present invention are also objects of the present invention.

The biodegradable nanogel of the present invention may be used alone by dissolving in an appropriate organic solvent, or may be used for various compositions by mixing with other macromolecular compounds according to the purpose of use. The medical device of the present invention should have the biodegradable nanogel of the present invention at least on a portion of the surface thereof that is used while in contact with vivo tissue or blood. That is, a composition containing the biodegradable nanogel of the present invention may be used as a surface treatment agent on a surface of a substrate constituting a medical device. Furthermore, at least a portion of the medical device may be constituted by the biodegradable nanogel or a composition thereof.

One embodiment of the present invention is the biodegradable nanogel of the present invention for suppressing a foreign-body reaction to blood or tissue, when the nanogel is used while in contact with in vivo tissue or blood before being decomposed.

The biodegradable nanogel of the present invention may be preferably used in medical applications. When the biodegradable nanogel of the present invention is used as a composition by being mixed with another macromolecular compound, etc., it can be used in an appropriate mixing ratio according to the purpose of use thereof. In particular, a composition having strengthened characteristics of the present invention can be formed by setting the ratio of the biodegradable nanogel of the present invention to at least 90 wt %. Additionally, a composition having increased characteristics of the present invention can be formed by setting the ratio of the biodegradable nanogel of the present invention to 50 to 70 wt %, depending on the application.

One embodiment of the present invention is a medical device containing the biodegradable nanogel of the present invention. Here, "medical device" includes implanted devices such as prostheses as well as devices that may temporarily come in contact with body tissues such as catheters, and is not limited to devices used inside the body. Furthermore, the medical device of the present invention is a device that is used in medical applications and has the polymer composition of the present invention on at least a portion of its surface. The surface of a medical device mentioned in the present invention means, for example, the surface of the material constituting the medical device that comes in contact with blood, etc. when the medical device is used, and the surface portions of pores in the material, etc.

In the present invention, the material and shape of the substrate that constitutes the medical device is not particularly limited, and may be, for example, a porous body, fiber, nonwoven fabric, granules, film, sheet, tube, hollow fiber, powder, etc. Examples of this material include natural macromolecules such as flax, and synthetic macromolecules such as nylon, polyester, polyacrylonitrile, polyolefin, halogenated polyolefin, polyurethane, polyamide, polycarbonate, polysulfone, polyether sulfone, poly(meth)acrylate, ethylene-vinyl alcohol copolymer, and butadiene-acrylonitrile copolymer, and mixtures thereof. Other examples include metals, ceramics, and composites thereof. Regardless of whether it is constructed from a plurality of substrates, it is desirable that the biodegradable nanogel of the present invention be provided on at least a portion of the surface thereof that comes in contact with blood, and preferably substantially the entire surface that comes in contact with blood.

The biodegradable nanogel of the present invention may be used as a material that constitutes the entire medical device used while in contact with in vivo tissue or blood, or a material that constitutes the surface portion thereof. Examples of medical devices used while in contact with in vivo tissue or blood include internally implanted prostheses or therapeutic instruments, extracorporeal circulation-type artificial organs, surgical suture thread, as well as catheters (catheters for circulatory organs such as vascular imaging catheters, guide wires, and PTCA catheters; catheters for digestive organs such as gastric catheters, gastrointestinal catheters, and esophageal catheters; and urologic catheters such as tubes, urethral catheters, and ureteral catheters). Furthermore, utilizing its biodegradability, the biodegradable nanogel according to the present invention is particularly preferably used in medical devices that dwell inside the body during therapy.

The biodegradable nanogel of the present invention may be used in a matrix material for a hemostatic agent, a body tissue adhesive material, a repair material for tissue regeneration, a carrier of a drug sustained-release system, a hybrid artificial organ such as an artificial pancreas or liver, an artificial blood vessel, a thrombolic material, or a scaffold for cell engineering.

In these medical devices, surface lubricity may be further provided so that insertion into blood vessels or tissues does not easily damage tissue. An excellent method for providing surface lubricity is to insolubilize an aqueous macromolecule and form a hydrophilic gel layer on the material surface. This method can provide a material surface having both biocompatibility and surface lubricity.

The biodegradable nanogel of the present invention is itself a material having excellent biocompatibility, but since a variety of bioactive substances can also be encapsulated in it, it can be used in a diversity of medical devices including not only blood filters but also blood preservation containers, blood circuits, indwelling needles, catheters, guide wires, stents, artificial lung equipment, dialysis equipment, endoscopes, etc.

Specifically, the biodegradable nanogel of the present invention may at least partially coat a substrate surface that constitutes a blood filter. Furthermore, the macromolecular compound of the present invention may coat at least a portion of a blood bag and the blood-contacting surface of a tube that connects to the blood bag. The biodegradable nanogel of the present invention may also coat at least a portion of the blood-contacting surface of an extracorporeal-circulation blood circuit constituted from an operating field-side blood circuit consisting of a tube, an arterial filter, a centrifugal pump, a hemoconcentrator, and a cardioplegia means.

The biodegradable nanogel of the present invention may also coat at least a portion of the blood-contacting surface of an indwelling needle assembly containing an internal needle having a sharp tip, an internal needle hub provided on the proximal side of the internal needle, a hollow external needle into which the internal needle can be inserted, a protector which is fit onto the internal needle and can move in the axial direction of the internal needle, and a connection means which connects the external needle hub and the protector. The biodegradable nanogel of the present invention may also coat at least a portion of the blood-contacting surface of a catheter constituted from a long tube and an adapter connected at the proximal end (the near side) thereof.

The biodegradable nanogel of the present invention may also coat at least a portion of the blood-contacting surface of a guide wire. The biodegradable nanogel of the present invention may also coat at least a portion of the blood-contacting surface of stents of various shapes, such as a stent provided with pores on the side surface of a hollow tubular body made of a metallic material or macromolecular material, or a stent made by braiding fibers made of macromolecular material or a wire made of metallic material and molding into a round cylindrical form.

The biodegradable nanogel of the present invention may also coat the exterior surface or exterior surface layer of a hollow fiber membrane of a hollow fiber membrane exterior blood perfusion type of artificial lung of the type in which a plurality of gas exchange porous hollow fiber membranes are held in a housing and blood flows to the exterior surface side of the hollow fiber membrane while oxygen-containing gas flows to the interior side of the hollow fiber membrane.

The biodegradable nanogel of the present invention may also coat at least a portion of the blood-contacting surface of a dialysis device having a dialyzed blood circuit which includes at least one blood drainage container which collects dialyzed blood, and a blood feeding means which feeds dialyzed blood and has the dialyzed blood container as a starting point and has the blood drainage container as the ending point.

Example 1

The present invention will be described in further detail below by citing examples, but the present invention is not limited to these examples. Unless otherwise stated, the drug used in the following examples is a commercially available product used in an unaltered state. In the following examples, the molecular weight distribution of the polymer obtained in each example was measured in the following manner.

Number-Average Molecular Weight ([Mn], Units: g/Mol)

Using standard polystyrene of known peak molecular weight, the number-average molecular weight (Mn) and weight-average molecular weight of the polymer were measured using gel permeation chromatography (GPC) ("TOSO HLC-8320GPC" manufactured by Toso Corporation; column structure: TSKguardcolumn SuperMP (HZ)-M, TSKgel SuperMultiporeHZ-M, four serial columns) corrected by the standard polystyrene. (Solvent: THF, temperature: 40° C., flow rate: 0.35 mL/min)

Molecular Weight Distribution ([Mw/Mn])

Using the values of weight-average molecular weight (Mw) and number-average molecular weight (Mn) determined by the above method, the molecular weight distribution was determined as the ratio thereof (Mw/Mn).

NMR Measurement

For structural analysis of the polymer, $^1$H-NMR measurement and $^{13}$C-NMR measurement were performed using an NMR measurement device (manufactured by Bruke; 400 MHz). Note that CDCl$_3$ ($^1$H: 7.26 ppm, $^{13}$C: 77.1 ppm) was used as the standard for chemical shift.

Synthesis of Single Aldehyde-Terminated Poly(Ethylene Glycol) (CHO-PEG-OH)

α-acetal-ω-hydroxyloyl-PEG (Mn=5,300,545 mg) was dissolved in 2.5 mL of THF, and then 2.5 mL of 1 N HCl was added, and this was stirred for 1 h at room temperature. It was then washed with water and extracted with chloroform, washed with saturate saline, and dehydrated with sodium sulfate, and then reprecipitated with diethyl ether. By freeze-drying using benzene, a white solid (CHO-PEG-OH) was obtained (yield: 422 mg (77%), $^1$H-NMR (400 MHz, chloroform-d, standard peak: underlined part) δ: 9.78-9.83 (2), 3.54-3.80 (1)).

Synthesis of PEG Graft Chitosan (PEG-g-CS)

Chitosan (CS (Koyo Chemical Co., Ltd., DAC50, lot 981028, Mw=234,000, Mn=93,000, Mw/Mn=2.5, deacetylation degree=54%), 80 mg, amino groups 2.38×10$^{-4}$ mol [quantity of amino groups per mass calculated from deacetylation degree]) was dissolved in 8 mL of Milli-Q water, and then the pH was adjusted to 6.5 by adding approximately 350 μL of 0.1 N NaOH. To this, powdered CHO-PEG-OH (410 mg, aldehyde groups 4.76×10$^{-5}$ mol [calculated from aldehydation rate 60%], 0.2 eq. vs. amino groups in CS) was added, and this was stirred at room temperature for 1 h. Then, sodium cyanoborohydride (29 mg, 10 eq. vs. aldehyde groups) was added, and this was stirred at room temperature for 24 h. The obtained solution was dialyzed for 1 d relative to water (fraction molecular weight: 12,000 to 14,000), and by freeze-drying, a white solid (PEG-g-CS) was obtained (yield: 435 mg (89%), $^1$H-NMR (400 MHz, deuterium oxide, standard peak: underlined part) δ: 2.83-3.00 (1), 2.67-2.82 (2)).

Note that when chitosan (Koyo Chemical Co., Ltd., DAC50HCl, lot 107311, Mw=1,046,000, Mn=157,000, Mw/Mn=6.7, deacetylation degree=47%) was used, the nanogel was difficult to form.

Synthesis of PEG and RADA Graft Chitosan (PEG/RADA-g-CS)

50 mg of PEG-g-CS (residual amino groups 1.87×10$^{-5}$ mol) was dissolved in 10 mL of Milli-Q water. To this was added approximately 35 μL of 0.1 N NaOH, to adjust the pH of the solution to 7.43. A separately prepared dry DMSO solution of N-succinimidyl 6-maleimidohexanoate (HL: hetero-linker) (12.0 mg, 3.74×10$^{-5}$ mol, 2.0 eq. vs. amino groups in CS) was added, and this was stirred for 3 h at room temperature (PEG/HL-g-CS). After stirring, it was purified by dialysis for 4 h in Milli-Q water using a dialysis membrane (fraction molecular weight 12,000 to 14,000). For structural analysis, a portion of the sample was collected as a powder by freeze drying. The maleimide modification rate was measured by $^1$H-NMR ($^1$H-NMR (400 MHz, deuterium oxide, standard peak: underlined part) δ: 6.94-7.04 (3), 2.86-3.02 (1), 2.75-2.86 (2)).

Synthesis of PEG/RADA-g-CS

FIG. 1A shows the structure of the PEG/RADA-g-CS. FIG. 1B shows "Grafted degree" indicates the proportion of modification of PEG and RADA relative to amino groups in the chitosan. Here, the quantity of amino groups in chitosan is defined based on the degree of acetylation. That is, taking deactylation into consideration, it is 54% when all amino groups are modified.

PEG was calculated from $^1$H-NMR analysis. HL (hetero-linker) is an abbreviation for N-succinimidyl 6-maleimidohexanoate. It is a molecule of low molecular weight for modifying maleimide groups on the chitosan framework. The maleimide group modification rate was also calculated from $^1$H-NMR analysis. Then, chitosan was modified with RADAGGGC (SEQ ID NO: 2) by reacting with maleimide groups, targeting cysteine of RADAGGGC (SEQ ID NO: 2). A micro BCA assay was used in quantitative analysis after RADA modification.

Then, the sample solution was diluted up to a total of 100 mL (final solvent concentration: 15 mM PBS), and 100 mL of RADAGGGC (SEQ ID NO: 2) aqueous solution (100 mL of 0.24 mg/mL added: 24 mg, 1.2 eq. vs. maleimide groups in CS) was added, and this was stirred at room temperature for 16 h (pH when stirred: 6.75). After stirring, it was purified by dialysis in Milli-Q water for 2 d using a dialysis membrane (fraction molecular weight 12,000 to 14,000). After dialysis, a white solid was obtained by freeze drying (PEG/RADA-g-CS). Only the amount required for IR analysis was collected from the dry sample of PEG/RADA-g-CS. The RADA modification rate was estimated from measurement of the peptide weight per unit sample weight using a micro BCA assay. PEG/RADA-g-CS aqueous solutions concentrated to target concentrations were used in subsequent experiments.

Evaluation of Aggregation Behavior of PEG/RADA-g-CS.

The evaluation of aggregation behavior of PEG/RADA-g-CS is shown in FIGS. 2A-2C. DLS measurements are shown in FIGS. 2A and 2B. SEM observation is shown in FIG. 2C. With PEG-g-CS, aggregate was first formed by modifying RADA without measuring scattering intensity. According to particle size measurement by DLS and observation by SEM, relatively monodisperse aggregates around 100 nm in diameter were obtained. Formation of aggregate based on RADA organization was suggested. There was a suggestion that the β-sheet structure in the aggregates was temporarily destroyed and uniformly re-aggregated by applying ultrasonic waves.

Evaluation of β-Sheet Structure in PEG/RADA-g-CS.

CD spectrum measurement revealed a negative cotton effect originating from the β-sheet structure of RADA in the PEG/RADA-g-CS, as shown in FIG. 3A. From CD spectrum measurement, a negative cotton effect originating from the β-sheet structure of RADA was observed in PEG/RADA16-g-CS. Fluorescence measurement also revealed formation of a β-sheet structure of RADA in the PEG/RADA-g-CS as shown in FIG. 3B. Thioflavine T final concentration was 50 μm and excitation wavelength was 460 nm. Concentration of PEG-g-CS, RADA, PEG/RADA-g-CS were each 1 mg/mL in PBS. From fluorescence measurement using thioflavine T as well, formation of a β-sheet structure in PEG/RADA-g-CS was ascertained.

Evaluation of encapsulation and release of FITC-BSA by PEG/RADA-g-CS aggregate is shown in FIGS. 4A-4B. FITC-BSA is 66 kDa and has 35 Cys residues in its structure, of which 34 Cys residues form —S=S—, as shown in FIG. 4A. FITC-BSA:RADA ratio=10:3 (wt), thus purification operation not performed. To improve aggregation capability in core of FITC-BSA (66 kDa, containing 35 Cys residues in structure, of which 34 form —S=S—), FITC-BSA and RADA were mixed (FITC-BSA:RADA ratio=10:3 (wt), Purification operation not performed) before mixing with PEG/RADA-g-CS. A Milli-Q aqueous solution of RADAGGGC (SEQ ID NO: 2) (0.5 mL, 1, 5, 10 eq. vs. FITC-BSA) was added to FITC-BSA (0.5 mg/mL in 2×PBS, 2.0 mL), and this was stirred at room temperature in a dark location for 16 h. At this time, since the concentration of FITC-BSA in the solution had become 0.4 mg/mL, it was used for RADAGGGC (SEQ ID NO: 2)-precoated FITC-BSA samples without a purification operation to remove unreacted RADAGGGC (SEQ ID NO: 2). For comparison, non-end-modified RADA16 (SEQ ID NO: 1) was mixed and stirred with FITC-BSA using the same weight ratio and operations.

RADA-precoated FITC-BSA was prepared by the above operations. Two samples were prepared, including a sample physically coated with FITC-BSA by using RADA16 (SEQ ID NO: 1), and a sample targeted at disulfide bonding with the Cys residues present in FITC-BSA (chemical modification to FITC-BSA) by using RADAGGGC (SEQ ID NO: 2). FITC-BSA contains 35 Cys residues per molecule, among which one is free Cys that is not involved in intramolecular disulfide bonding. Thus, RADAGGGC (SEQ ID NO: 2) was added, targeted at disulfide bond formation with that Cys. It has not been confirmed that RADAGGGC (SEQ ID NO: 2) can actually chemically modify FITC-BSA by this RADA precoating technique, but the effect of RADA precoating was evaluated by subsequent encapsulation and release testing and structural stability testing (FIGS. 5-10).

Figure 5A:
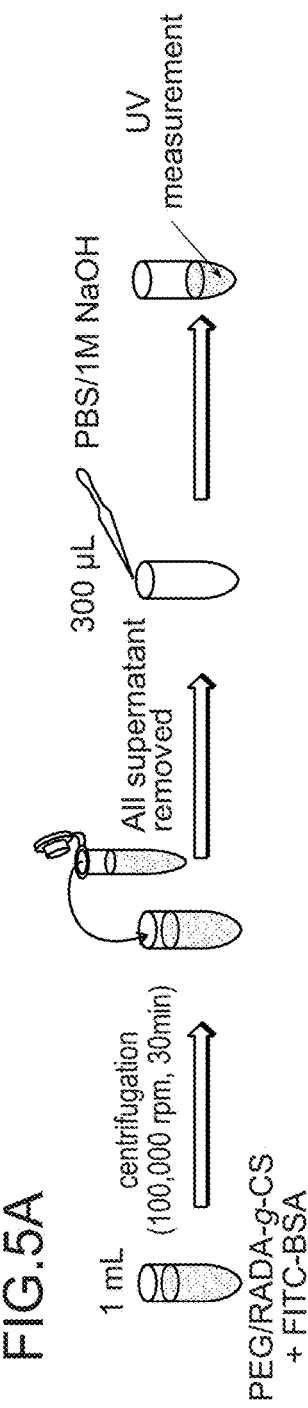
FIGS. 5A-5B present examples of evaluation of encapsulation and release behavior of FITC-BSA on PEG/RADA-g-CS aggregate.
Figure 5B:
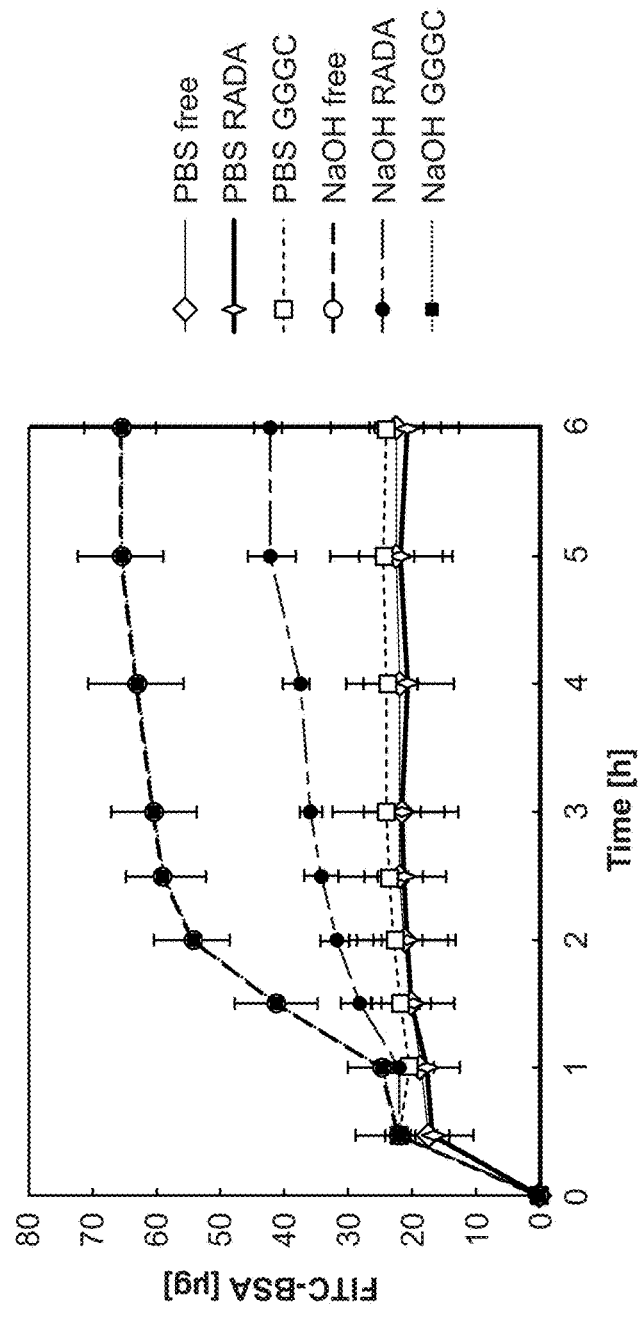

Evaluation of encapsulation and release behavior of FITC-BSA on PEG/RADA-g-CS aggregate are shown in FIGS. 5A-5B. Repease behavior measurement results are shown in FIG. 5B. In PBS, where disintegration of the aggregate is not observed, a certain amount of FITC-BSA was released, after which no further release was observed. In NaOH, where disintegration of the aggregate is suggested, it was gradually released for up to 6 hours.

Figure 6A:
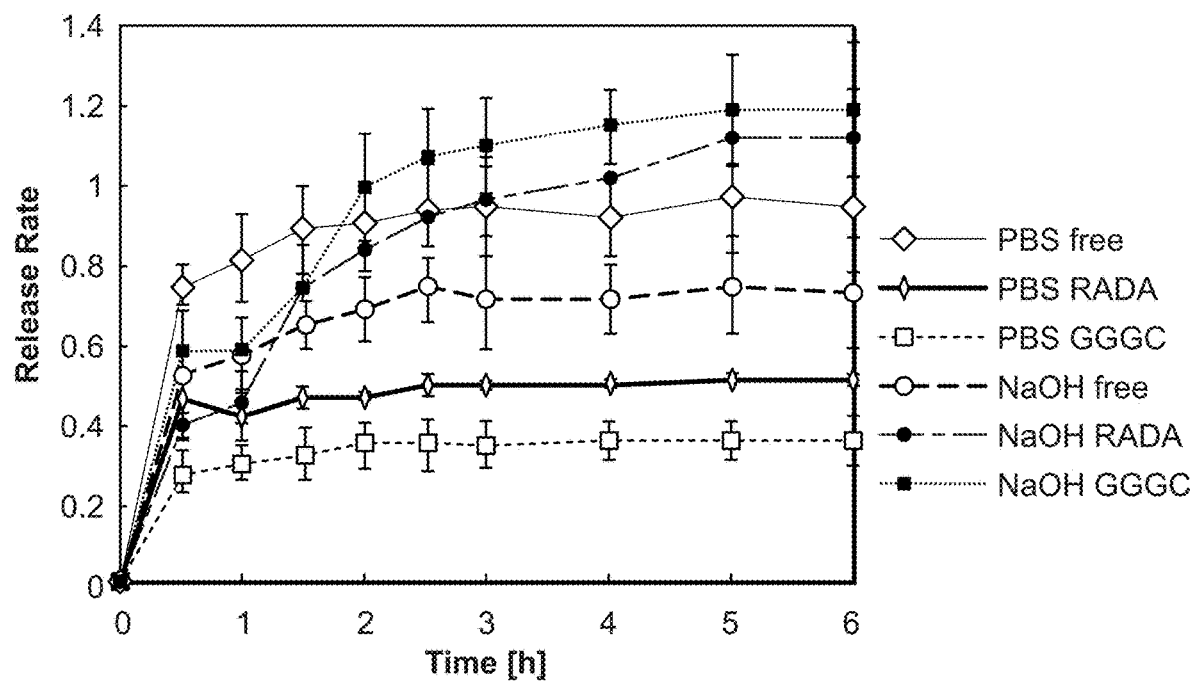
FIGS. 6A-6B present examples of evaluation of encapsulation and release behavior of FITC-BSA on PEG/RADA-g-CS aggregate.
Figure 6B:
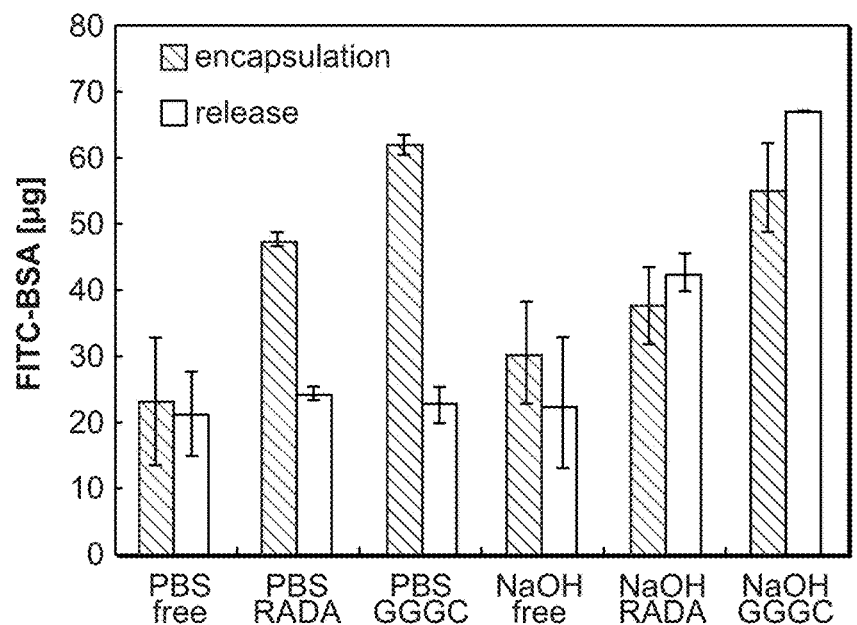
Figure 7:
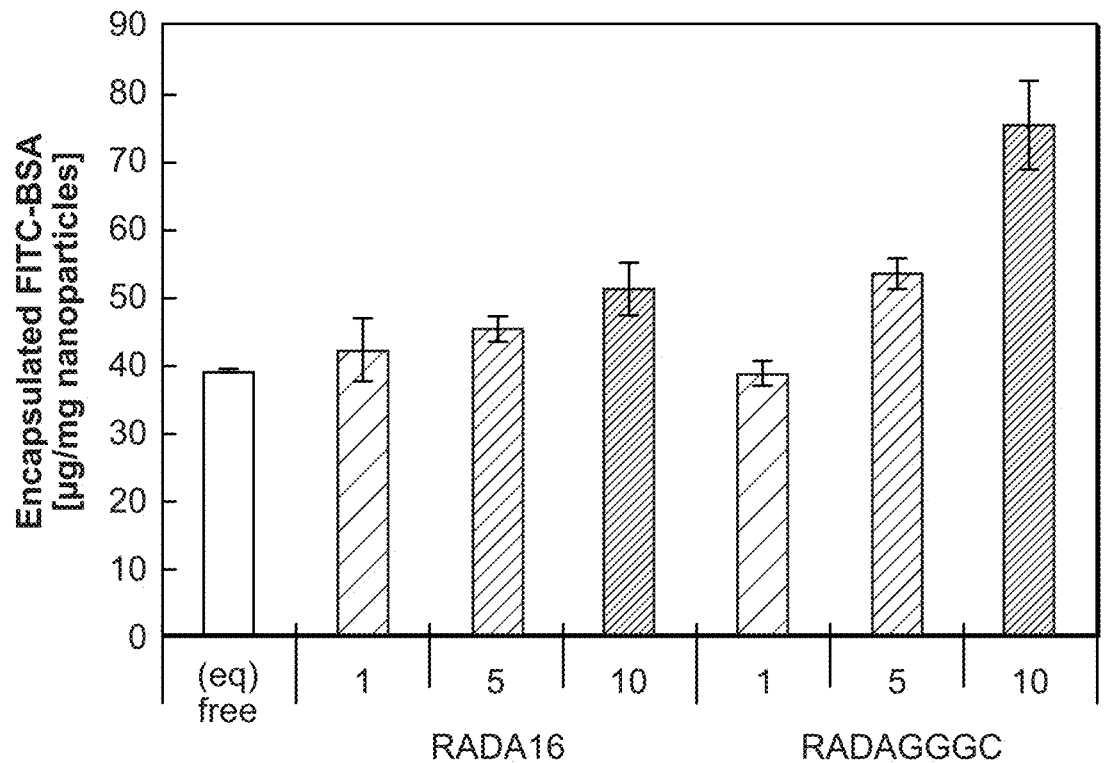
FIG. 7 presents an example of encapsulated weight measurement in an aggregate when RADA precoating equivalents is varied.
Figure 8:
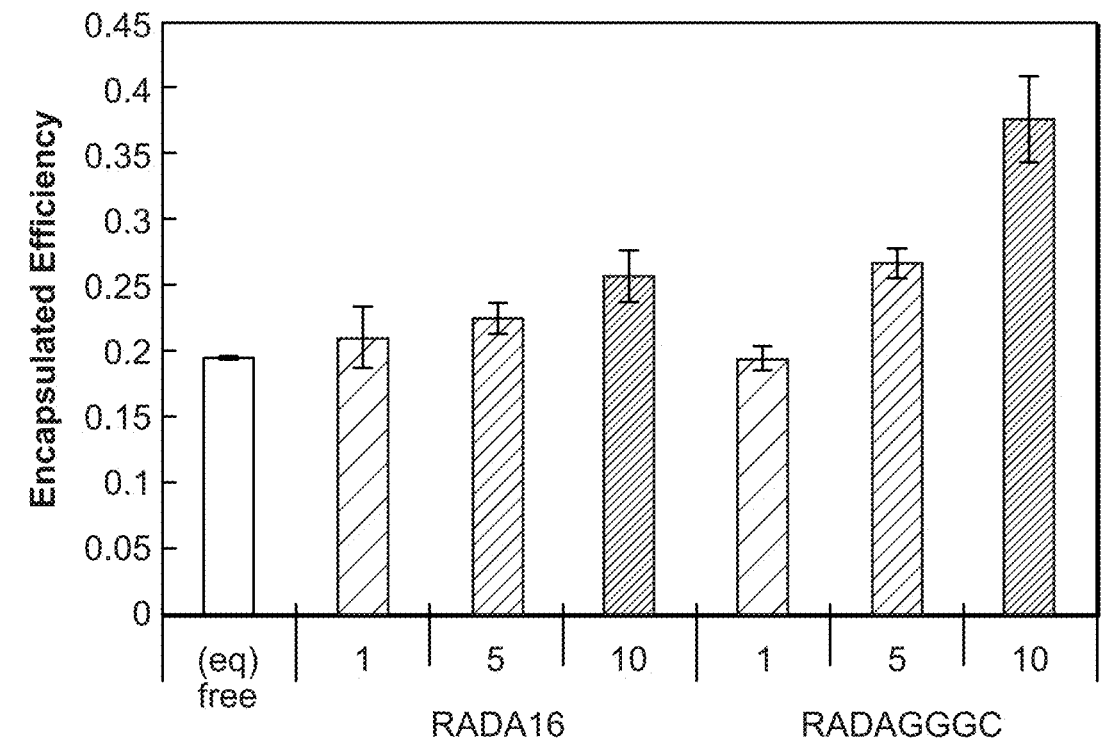
FIG. 8 presents an example of encapsulated weight measurement in an aggregate relative to added FITC-BSA.
Figure 10:
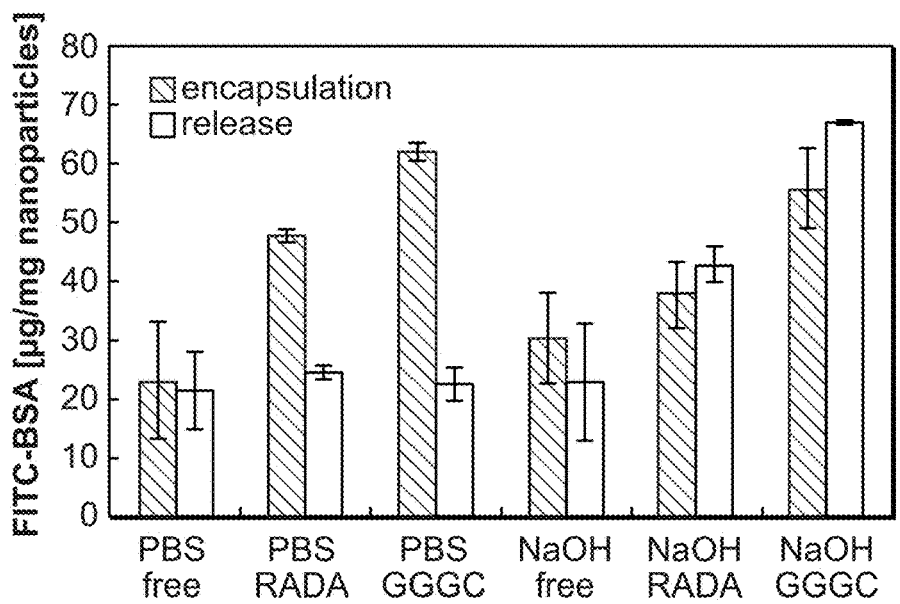
FIG. 10 presents an example of the encapsulated/released substance balance.
Figure 11A:
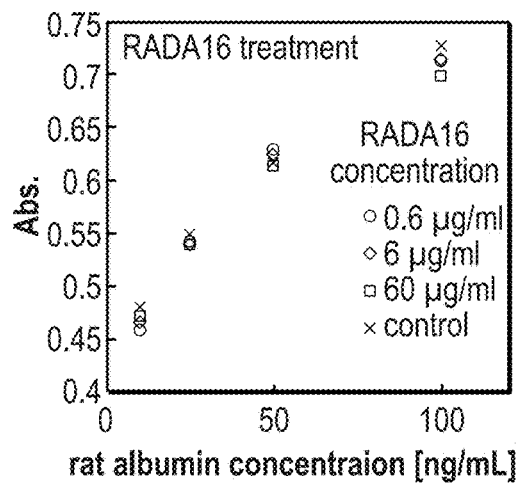
FIGS. 11A-11B present examples of structural stability evaluation of RADA-modified albumin.
Figure 11B:
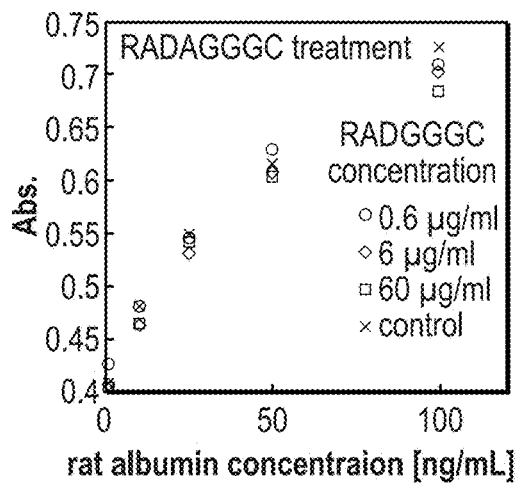

FIGS. 6A-6B show evaluation of encapsulation and release behavior of FITC-BSA on PEG/RADA-g-CS aggregate. Encapsulated weight on aggregate was improved by pre-mixing RADA16 (SEQ ID NO: 1), RADAGGGC (SEQ ID NO: 2) with FITC-BSA. In the system in which release behavior to PBS was measured, the release weight held constant regardless of encapsulated weight. In the system in which release behavior to NaOH was measured, it is thought that the total encapsulated weight was released as the aggregate disintegrated. FITC-BSA encapsulated weight on aggregate can be improved by mixing with RADA. It was suggested that it could result in a carrier that releases FITC-BSA as the aggregate disintegrates.

The molecular recognition function through RADA modification was evaluated using an ELISA assay. These are the ELISA measurement results using untreated albumin as a control. In albumin treatment with either RADA16 (SEQ ID NO: 1) or RADAGGGC (SEQ ID NO: 2), the ELISA measurement results were about the same as the control. Thus, RADA precoating was achieved without structural variation of the protein, and encapsulation without structural variation of the protein was also achieved in nanogel encapsulation using this technique (FIGS. 11A-12B).

Evaluation of Encapsulation and Release of FITC-Lysozyme by PEG/RADA-g-CS Aggregate.

Synthesis of FITC-lysozyme (Robeson, J. L. et al. Langmuir. 1996, 12, 6104-6113, Takano, M. et al. Eur. J. Pharmacol. 2004, 502, 149-155)

First, 50 mg ($3.57 \times 10^{-6}$ mol) of lysozyme was dissolved in 30 mL of 100 mM borate buffer of pH 9.2 (pH adjusted by adding 1 M NaOH to boric acid solution (final concentration of boric acid=100 mM)). To this was added 550 μL of 1.0 mg/mL FITC aqueous solution ($1.41 \times 10^{-6}$ mol, 0.55 mg, 0.4 eq. as molar equivalents vs. lysozyme), and this was stirred at room temperature for 1 h. Then, after dialysis for 2 d in PBS, it was ascertained by UV spectrum measurement without performing overnight solvent exchange (dialysis total for 3 d) that no absorption originating from FITC was seen in the dialysis membrane external solution. After dialysis completion, filtration was performed using a syringe filter with a pore diameter of 1.0 μm to remove insolubilized matter from the dialysis membrane internal solution. After filtration, the respective concentrations of FITC and lysozyme were measured (see below for details), and the recovered solution was diluted using PBS to 0.5 mg/mL, which is the concentration when used.

Determination of Concentrations of Compounds in FITC-Lysozyme.

For FITC measurement, light absorbance measurement was employed because fluorescence intensity varies greatly and measurability is poor depending on elapsed time and the type of solvent.

(A) Measurement of FITC in FITC-Lysozyme—UV Spectrum Measurement—

1. To measure FITC, the UV spectra of PBS solutions of FITC [0/5/10/25/50 ($\times 10^{-6}$ M)] were measured, and a calibration curve was created from absorbance at 495 nm.

2. The UV spectrum was measured for a sample diluted 10× with PBS so that the absorbance of the sample solution was in a measurable range.

3. Using the calibration curve created in step 1, the FITC concentration in the sample solution was calculated from the absorbance at 495 nm of the sample solution.

(B) Measurement of Lysozyme in FITC-Lysozyme—BCA Assay—

1. For a calibration curve, PBS solutions of lysozyme were prepared [0/0.25/0.50/0.75/1.0/1.5/2.0 (mg/mL)].

2. To ascertain that FITC is not a substance harmful to the BCA assay, PBS solutions of FITC were prepared [0/10/25/50/100 (µg/mL)].

3. BCA assays of the calibration curve solutions and sample solutions prepared in steps 1 and 2 above were performed according to the kit manufacturer's procedure.

(C) Determination of Respective Concentrations of FITC and Lysozyme

1. For FITC, the FITC concentration in the sample solution was calculated using the calibration curve from the absorbance at 495 nm of the sample solution obtained in experiment (A).

2. For lysozyme, because it was found in experiment (B) that FITC reacts in the BCA assay, the lysozyme concentration was determined from a lysozyme calibration curve after subtracting, as background, the absorbance equivalent to the FITC concentration calculated in experiment (A) in the FITC calibration curve of experiment (B).

Evaluation of structural stability of FITC-lysozyme

By the above operations, CD spectra were measured for the sample solution by which lysozyme concentration was calculated and a non-FITC-modified lysozyme solution (in this measurement, the lysozyme concentration was adjusted to 0.05 mg/mL). CD spectrum measurement conditions Starting wavelength: 300 nm
Ending wavelength: 205 nm
Number of approximations: 3
Data interval: 0.5 nm
Response: 1 sec
Bandwidth: 1.0 nm
Light path length: 1 cm
Sensitivity: 50 mdeg
Operating sensitivity: 200 nm/min The results of measuring each compound in the sample solution are shown in Table 1 and FIGS. 12A-12B.

TABLE 1

| Modification conditions | Compound name | Concentration [mol/L] | Solvent qty. [mL] | Mass [mg] | Yield [%] | FITC modification rate [mol/mol lysozyme] |
|---|---|---|---|---|---|---|
| pH 9.2 | Lysozyme | 6.47 × 10-5 | 30 | 27.2 | 54 | 0.90 |
|  | FITC | 5.83 × 10-5 |  | 0.68 | 123 |  |

When the CD spectra were measured after matching the lysozyme concentrations of the synthesized FITC-lysozyme and native lysozyme, agreement of the waveforms and of the intensities of the spectra was ascertained. Therefore, it is believed that the FITC-lysozyme synthesized in this experiment was not denatured by FITC modification.

Encapsulation and release of the synthesized FITC-lysozyme in an aggregate was evaluated using the calibration curve from FITC absorbance.

RADA Precoating of FITC-Lysozyme

FITC-lysozyme is 14 kDa and has 8 Cys residues in its structure, all of which form —S=S—.

RADAGGGC (SEQ ID NO: 2) (Milli-Q aqueous solution, 0.5 mL, 1, 5, 10 eq. vs. FITC-lysozyme) was added to FITC-lysozyme (0.5 mg/mL in 2×PBS, 2.0 mL), and this was stirred at room temperature in a dark location for 16 h. At this time, since the concentration of FITC-lysozyme in the solution had become 0.4 mg/mL, it was used for RADAGGGC (SEQ ID NO: 2)-precoated FITC-lysozyme samples without a purification operation to remove unreacted RADAGGGC (SEQ ID NO: 2). For comparison, non-end-modified RADA16 (SEQ ID NO: 1) was mixed and stirred with FITC-lysozyme using the same weight ratio and operations.

The RADA aqueous solution concentration and conditions used in precoating are shown below.

TABLE 2

| Added equivalents* [X eq. vs. 1 mol FITC-lysozyme] | RADA aqueous solution concentration [mg/mL] | Solvent concentration at precoating | Weight ratio relative to FITC-lysozyme [FITC-Lysozyme:RADA = 1:X] |
|---|---|---|---|
| 10 | 3.0 | 1.6X PBS | 1.5 |
| 5 | 1.5 |  | 0.75 |
| 1 | 0.3 |  | 0.15 |

*"Added equivalents" means the added molar weight of RADA relative to 1 mol of lysozyme.

RADA-precoated FITC-lysozyme was prepared by the above operations. Two samples were prepared, including a sample physically coated with FITC-lysozyme by using RADA16 (SEQ ID NO: 1), and a sample targeted at disulfide bonding with the Cys residues present in FITC-lysozyme (chemical modification to FITC-lysozyme) by using RADAGGGC (SEQ ID NO: 2). Because FITC-lysozyme contains 8 Cys residues per molecule and all of them are involved in intramolecular disulfide bonding, there is no free Cys, but precoating was performed targeted at RADAGGGC (SEQ ID NO: 2) bonding with lysozyme by an exchange reaction via thiol in the Cys residues that form disulfide bonds. Similar to FITC-BSA, it has not been confirmed that RADAGGGC (SEQ ID NO: 2) can chemically modify lysozyme by this RADA precoating technique, but the significance of RADA precoating and the lysozyme thereof were evaluated by subsequent encapsulation and release testing and bacteriolytic activity testing.

1. The concentration of a Milli-Q aqueous solution of PEG/RADA-g-CS was adjusted to 2.0 mg/mL.

2. FITC-BSA precoated with RADA16 (SEQ ID NO: 1) or RADAGGGC (SEQ ID NO: 2) (RADA precoating equivalent amount: 1, 5, 10 eq. vs. FITC-lysozyme) and non-precoated FITC-lysozyme were adjusted so that the FITC-lysozyme concentration was 0.4 mg/mL (final solvent concentration: 1.6×PBS).

3. The solutions of the above steps 1 and 2 were added to microtubes in equal amounts of 750 µL each and mixed, and they were subjected to ultrasound using a bath sonicator for 30 min. (Concentration when encapsulated: PEG/RADA-g-CS: 1.0 mg/mL, FITC-lysozyme: 200 µg/mL)

4. After ultrasonic treatment was completed, 1 mL of each of the solutions was centrifuged at 100,000 rpm for 30 min, the supernatant solution was removed, and the entire amount was fractionated.

5. The supernatant samples were added in an amount of 100 µL to 96-well plates, and absorbance was measured using a microplate reader. [Measurement wavelength: 494 nm]

6. To measure the release behavior of the three samples of non-RADA-precoated FITC-lysozyme and FITC-lysozyme precoated with 10 equivalents of RADA16 (SEQ ID NO: 1) or RADAGGGC (SEQ ID NO: 2), 300 µL of fresh PBS or 1 M NaOH, which is known to accelerate aggregate disintegration, was added to each centrifuge tube.

7. Absorbance of the FITC-lysozyme released into the solvent was measured at fixed time intervals (100 µL was added to a 96-well plate, and absorbance at 494 nm was measured, and after measurement, the used 100 µL sample was returned in its entirety to the centrifuge tube).

Results are shown in FIGS. 14 to 17.

First, encapsulated weight will be discussed. Compared to the non-RADA-precoated FITC-lysozyme, an improvement in encapsulated weight was observed in the samples pre-coated with RADA. Furthermore, it was found that this lysozyme with improved encapsulated weight could be further improved by increasing the equivalents of RADA added. Additionally, a comparison of the two types of RADA revealed that the encapsulated weight was more greatly improved in RADAGGGC (SEQ ID NO: 2), in which chemical modification of disulfide bonding to the FITC-lysozyme was suggested, than in RADA16 (SEQ ID NO: 1), which physically coats the FITC-lysozyme. This result is thought to be due to the fact that it was efficiently encapsulated via intermolecular β-sheet structure formation on the RADA core of the PEG/RADA-g-CS aggregate by the technique of precoating FITC-lysozyme with RADA. The above results exhibit a trend similar to that of FITC-BSA performed previously, and suggest that the RADA precoating technique is applicable to improvement of encapsulated weight of various proteins.

Next, release weight will be discussed. In measuring the release behavior of FITC-lysozyme from an aggregate in this experiment, two types of solvent were used, including PBS and 1 M NaOH, which is known to accelerate aggregate disintegration. The upper row shows graphs of release rate, as the ratio of release weight relative to encapsulated weight. The lower row shows graphs with the weight of released FITC-lysozyme on the vertical axis. Comparing the two types of solvent, substantially no release of FITC-lysozyme was measured in PBS in which no disintegration of the aggregate is observed, while under basic conditions in which disintegration of the aggregate is suggested, approximately 60% of the encapsulated weight was released as the aggregate disintegrated. Comparing the release of each sample in 1 M NaOH, slow release was achieved in RADA-precoated FITC-BSA compared to non-RADA-modified BSA, and further, lysozyme was more prominent in RADAGGGC (SEQ ID NO: 2) than in RADA16 (SEQ ID NO: 1). This is thought to be a result that correlates with the results of encapsulated weight, where it is thought that BSA is efficiently encapsulated in the aggregate core via β-sheet structure formation through the self-organizing characteristics of RADA.

Considering the balance of encapsulated and released substances, approximately 80% of the encapsulated weight was released in 6 hours in the system that used 1 M NaOH. In the system that used FITC-BSA, substantially the entire amount was released in 6 hours. Thus, it is thought that some kind of specific bonding between PEG/RADA-g-CS and lysozyme is involved in this case. It is known that in general, protein release behavior in bulk gels that use RADA depends greatly on the molecular weight of the protein, and that it is not really affected by electrical charge (Koutsopoulos, S. et al. PNAS. 2009, 106, 4623-4628, Hosseinkhani, H. et al. Chem. rev. 2013, 113, 4837-4861). For this reason, it was believed that more rapid release behavior would be obtained with FITC-lysozyme, which has a lower molecular weight than FITC-BSA, than with FITC-BSA. However, in the results obtained in these experiments, release in PBS was greatly suppressed even in non-RADA-precoated FITC-lysozyme, which is different from the characteristics exhibited by RADA microgel. Because this aggregate contains PEG and CS as constituent elements in addition to RADA, it is believed that such results were obtained due to specific bonding of lysozyme to either of them, but details are currently being discussed and investigated.

Functional Evaluation of RADA-Precoated FITC-Lysozyme

Preparation of *Micrococcus* Solution

Using 1×PBS (137 mM NaCl, 2.7 mM KCl, 8.0 mM $Na_2HPO_4.12H_2O$, 1.5 mM $KH_2PO_4$), a 150 µg/mL solution of *Micrococcus* (*Micrococcus lysodeikticus*, ATCC no. 4698) was prepared. It was diluted with PBS to a final concentration of 100 µg/mL, and the UV spectrum of the solution was measured using a cell with a light path length of 1 cm. It was ascertained that absorbance at 450 nm was 0.6 to 0.7. In analysis of bacteriolytic activity of lysozyme using *Micrococcus*, a final concentration of 100 µg/mL was employed.

Evaluation of bacteriolytic activity of lysozyme (Davies, R. C. et al. BIOCHIMICA ET BIOPHYSICA ACTA 1968, 178, 294-503)

1. 666 µL of *Micrococcus* solution (150 µg/mL) and 234 µL of 1×PBS were added to a black cell with a light path length of 1 cm.

2. To this was added 100 µL of a separately prepared lysozyme sample. Note that the peptide-precoated lysozyme sample was prepared by mixing lysozyme and the peptide solution and then reacting for 16 h in a dark location, which was then used in evaluation of bacteriolytic activity.

3. After the lysozyme sample was added, it was quickly pipetted 10 times, immediately after which measurement was started and absorbance at 450 nm was monitored.

4. The rate of decrease of absorbance at 450 nm for 60 s after the start was calculated from the slope of linear approximation, and this was taken as the bacteriolytic activity of lysozyme.

5. The bacteriolytic activity survival rate of lysozyme due to peptide coating was calculated by comparing the bacteriolytic activity of peptide-precoated samples (precoating conditions included three lysozyme:RADA or GGGC-RADA ratios of 1:1, 1:10, 1:100), taking the activity of peptide-free lysozyme as 1. Here, the total volume of sample was 1000 µL, and the final concentrations were standardized to 100 µg/mL for *Micrococcus* and 6 µg/mL for lysozyme.

Figure 12A:
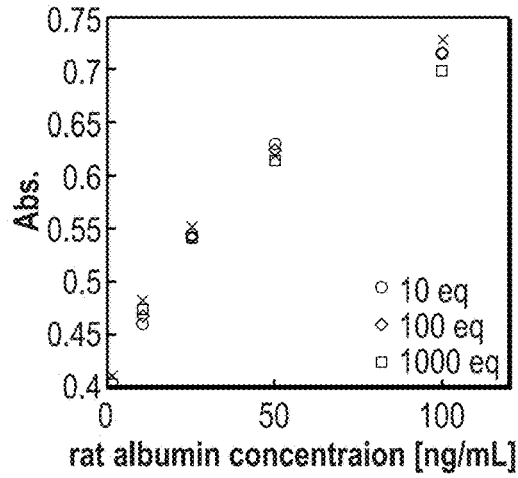
FIGS. 12A-12B present examples of structural stability evaluation of RADA-modified albumin.
Figure 12B:
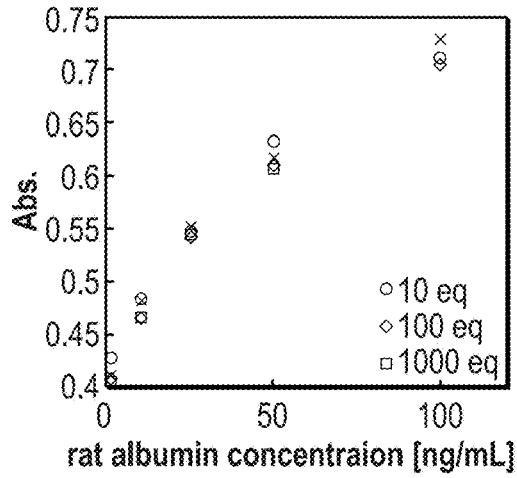
Figure 13:
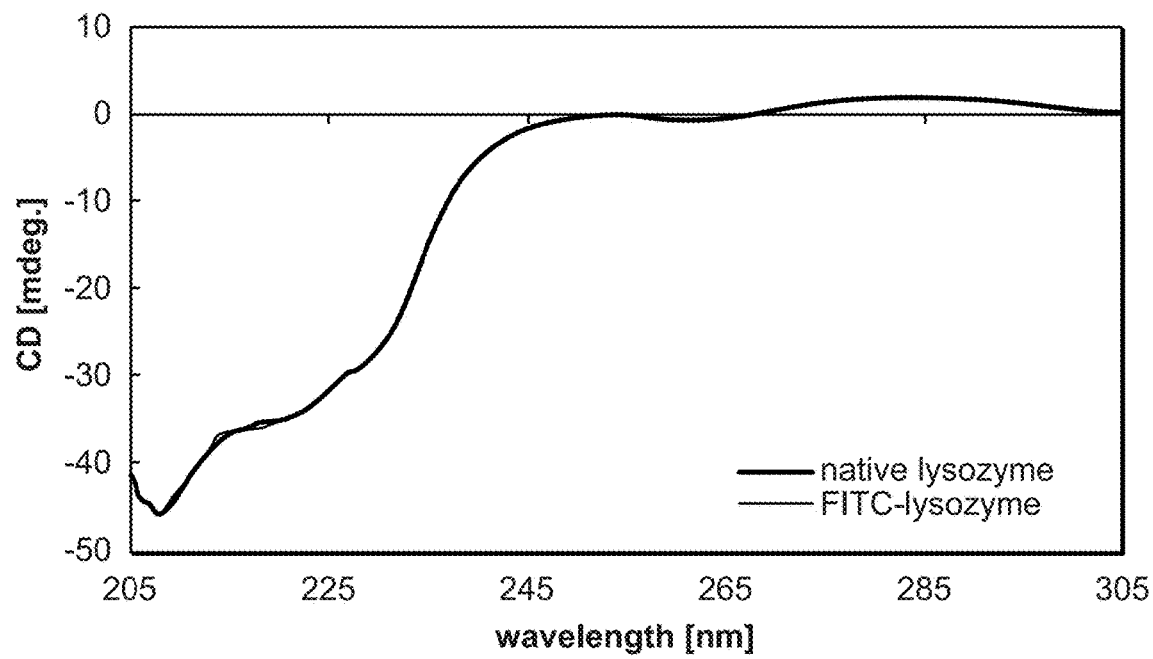
FIG. 13 presents an example of measuring the CD spectrum of FITC-lysozyme.
Figure 14:
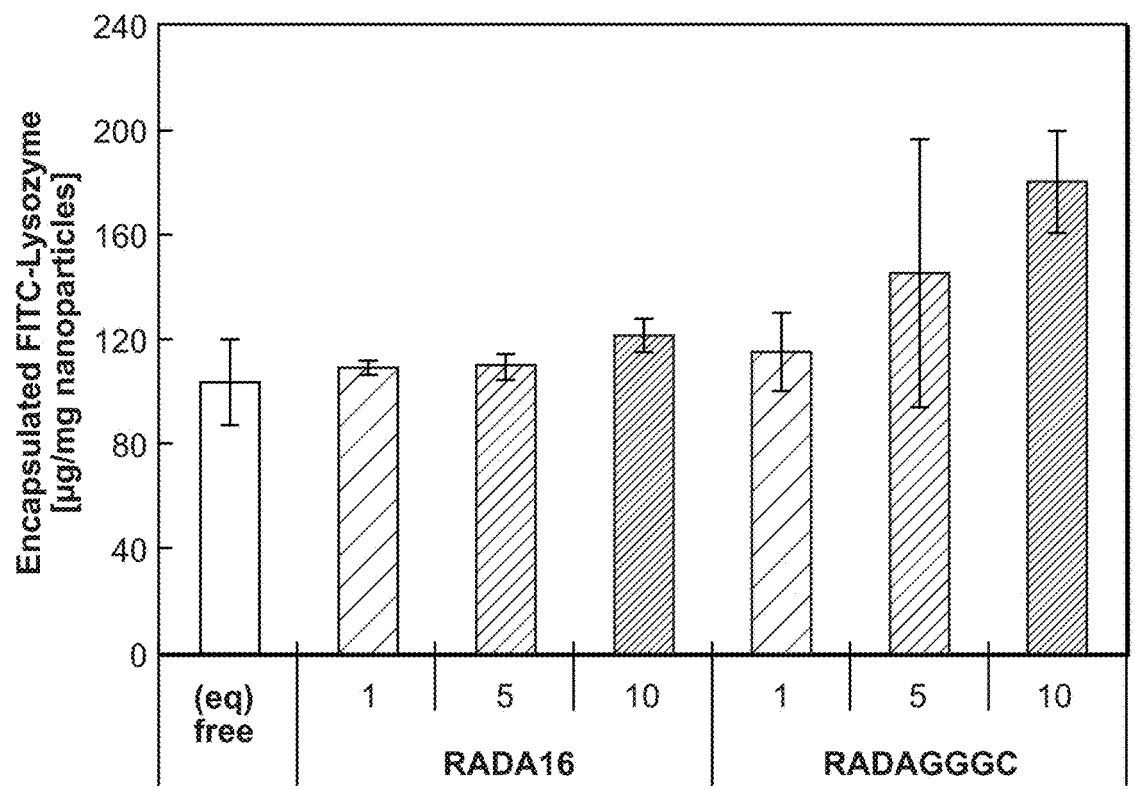
FIG. 14 presents an example of encapsulated weight measurement in FITC-lysozyme when RADA precoating equivalents is varied.
Figure 15:
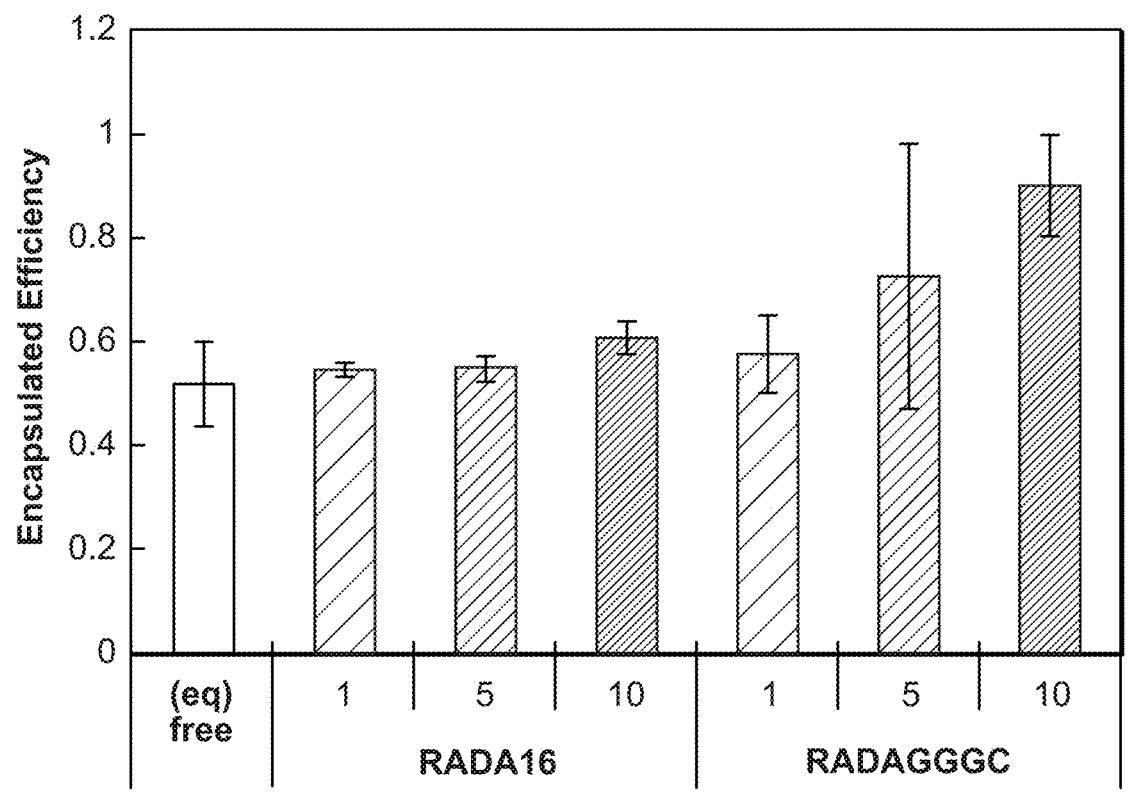
FIG. 15 presents an example of encapsulation efficiency measurement in an aggregate relative to added FITC-lysozyme.
Figure 16A:
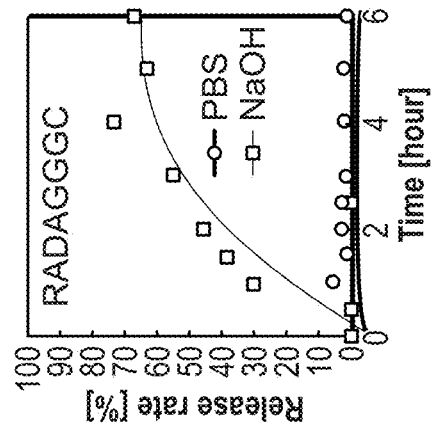
FIGS. 16A-16F present examples of release behavior of FITC-lysozyme.
Figure 16B:
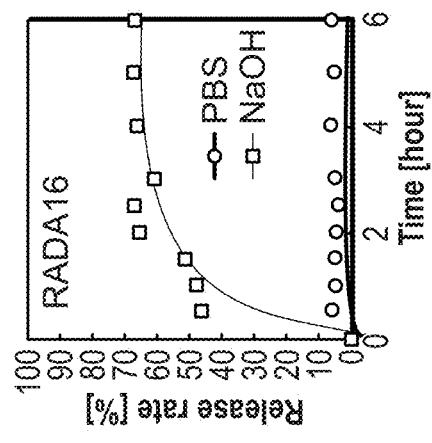
Figure 16C:
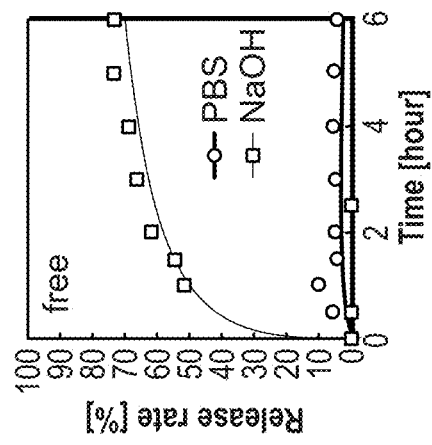
Figure 16D:
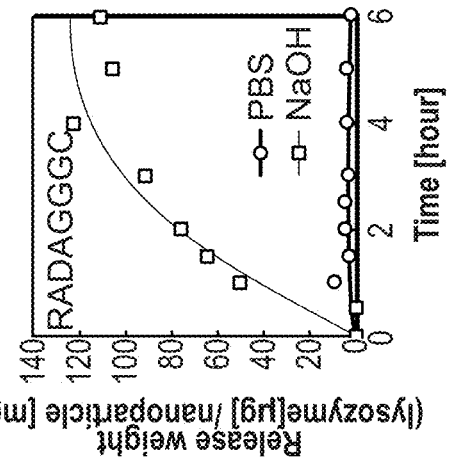
Figure 16E:
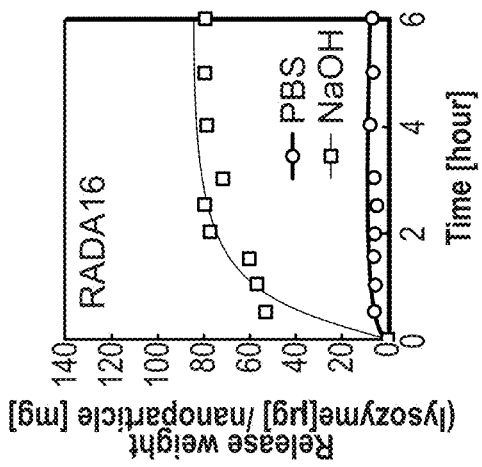
Figure 16F:
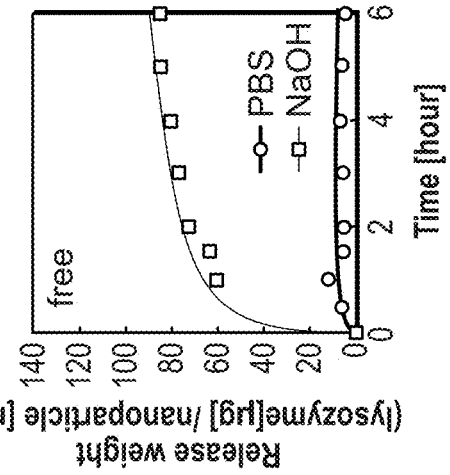
Figure 17:
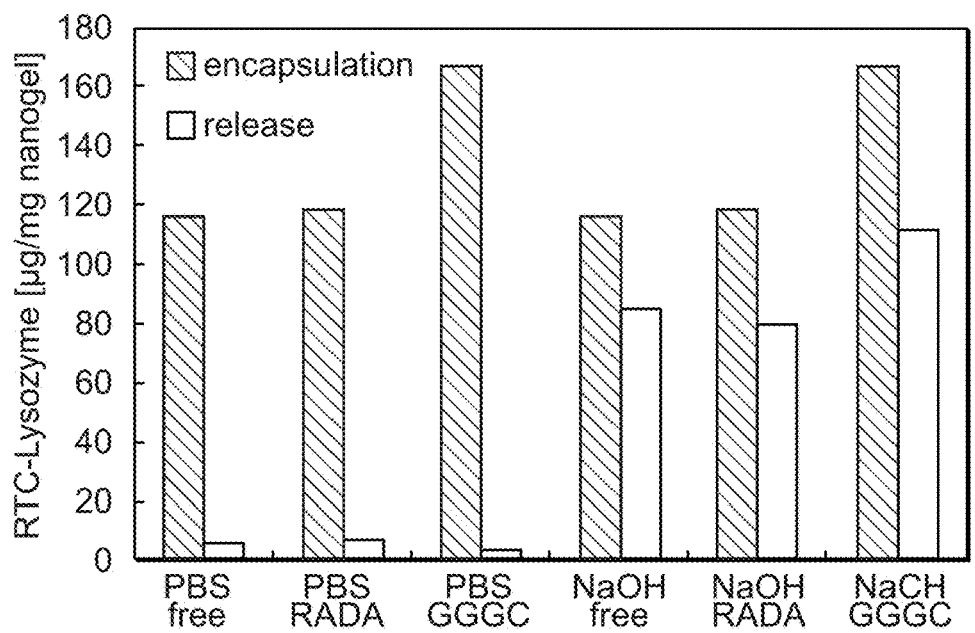
FIG. 17 presents an example of the encapsulated/released substance balance of FITC-lysozyme.
Figure 18:
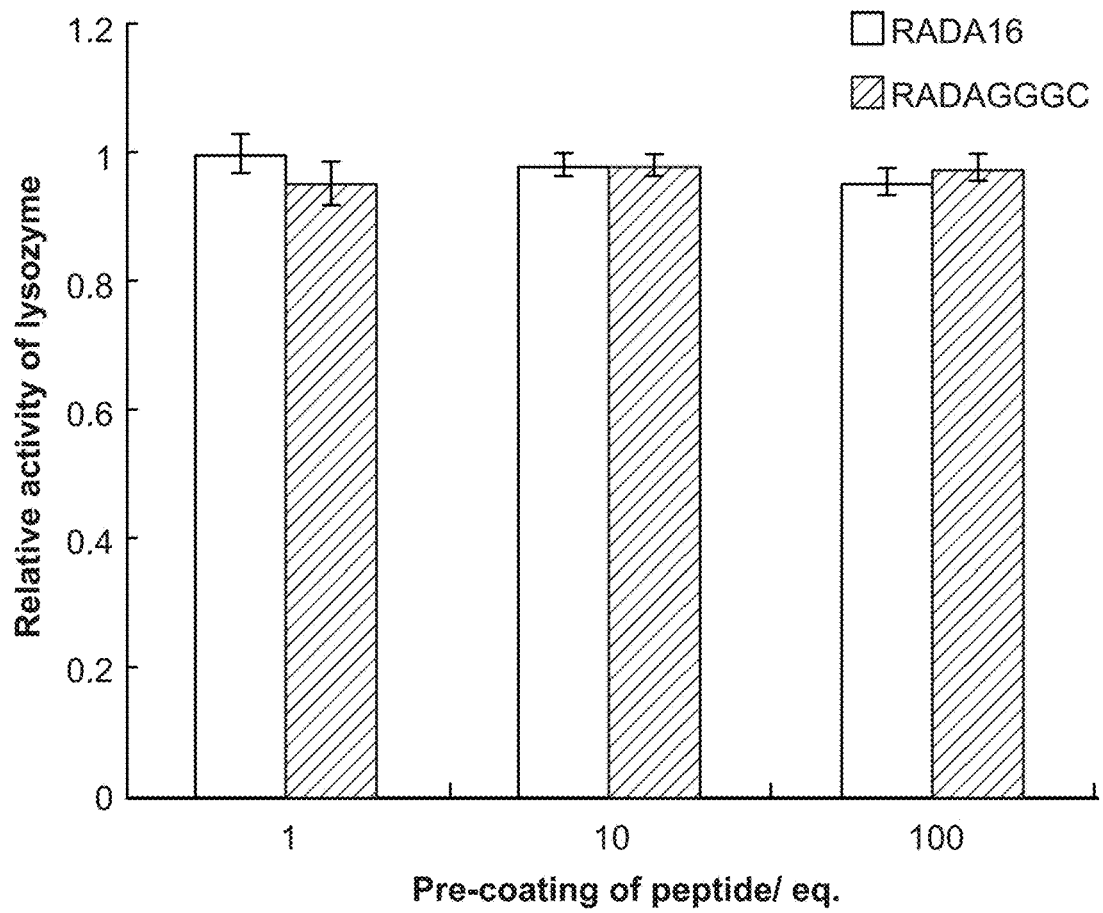
FIG. 18 presents an example of the bacteriolytic activity of RADA-precoated lysozyme.

FIGS. 12A-12B show the bacteriolytic activity of peptide-coated lysozyme when the bacteriolytic activity of lysozyme is taken as 1. It was ascertained that activity of lysozyme was stably maintained by precoating with RADA16 (SEQ ID NO: 1) or RADAGGGC (SEQ ID NO: 2). This result suggests that it is possible to stably and efficiently encapsulate a peptide coat on a protein in a nanogel while maintaining protein activity.

The nanogel of the present invention is useful for protein delivery.

The invention claimed is:

1. A nanogel comprising a self-organizing peptide, a chitosan, and polyethylene glycol, wherein the self-organizing peptide is RADARADARADARADAGGGC (SEQ ID NO:2).

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Artificial Sequence
<220> FEATURE:
<223> OTHER INFORMATION: synthesized peptide

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 20
<212> TYPE: PRT
<213> ORGANISM: Artificial Sequence
<220> FEATURE:
<223> OTHER INFORMATION: synthesized peptide

<400> SEQUENCE: 2

Arg Ala Asp Ala Arg Ala Asp Ala Arg Ala Asp Ala Arg Ala Asp Ala
1               5                   10                  15

Gly Gly Gly Cys
            20
```